United States Patent [19]

Ness

[11] 4,186,744
[45] Feb. 5, 1980

[54] SEPARABILITY MEMBER TO ALLOW DISPOSABLE DIAPER OPENINGS AND RE-FASTENINGS

[75] Inventor: Irving S. Ness, Princeton, N.J.

[73] Assignee: Johnson & Johnson, New Brunswick, N.J.

[21] Appl. No.: 847,458

[22] Filed: Oct. 31, 1977

Related U.S. Application Data

[63] Continuation of Ser. No. 709,748, Filed Jul. 29, 1976, abandoned.

[51] Int. Cl.² .................... A61F 13/16; A43C 11/00
[52] U.S. Cl. ................................. 128/287; 128/284
[58] Field of Search ............... 128/287, 284, 290 R; 428/343, 41, 382, 77; 24/DIG. 11, 73 VA, 67 R; 229/49, 85

[56] References Cited

U.S. PATENT DOCUMENTS

| 3,138,476 | 6/1964 | Phipps | 428/343 X |
| 3,503,568 | 3/1970 | Galley | 24/DIG. 1 |
| 3,943,609 | 3/1976 | Egan, Jr. | 128/287 X |
| 3,951,149 | 4/1976 | Ness et al. | 128/287 |
| 3,967,624 | 7/1976 | Milnamow | 128/287 |

*Primary Examiner*—Stephen C. Pellegrino

[57] ABSTRACT

An individualized separability member is used in combination with the adhesive portion of a closure tab on a disposable diaper to allow separation of the closure tab from the diaper surface and re-fastening to the diaper. The separability member includes a strip of material having a non-adhesive surface with adhesive release areas on the ends thereof for mating with the adhesive portion of the tab. The other surface is adhesively treated for fastening to the diaper. After fastening, the adhesive tab is detachable from the separability member by peeling the two apart.

6 Claims, 4 Drawing Figures

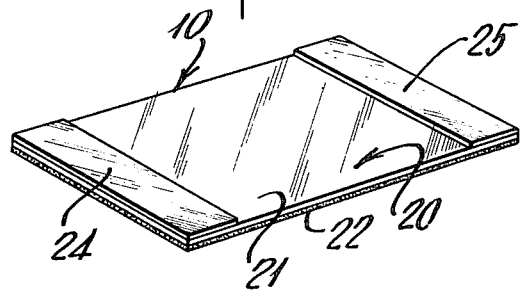
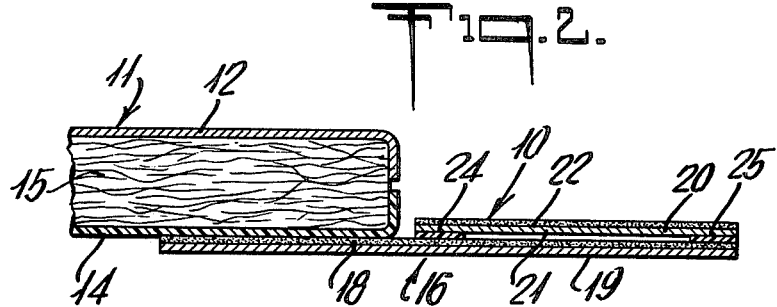
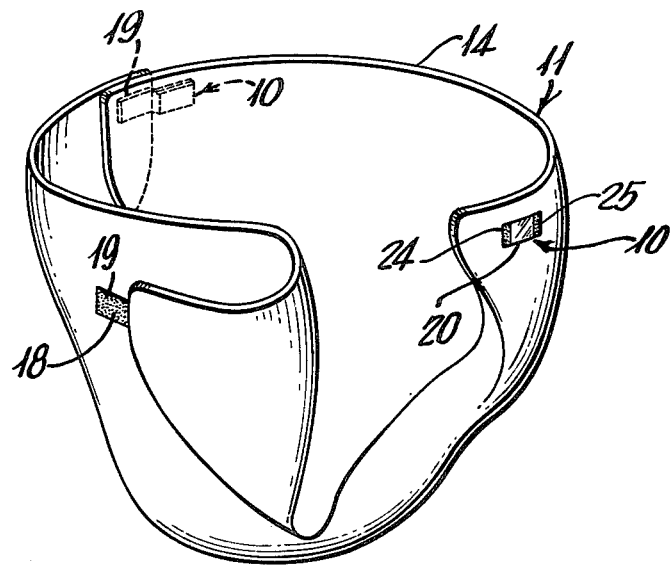
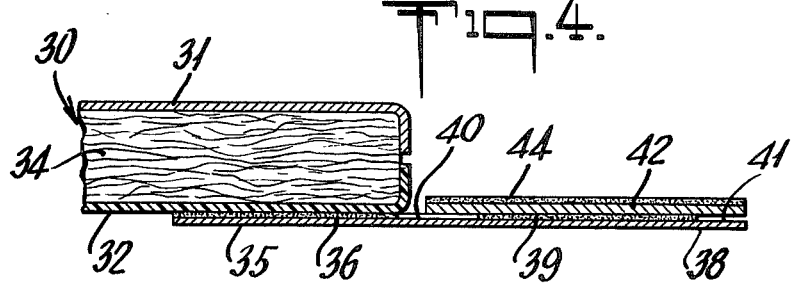

SEPARABILITY MEMBER TO ALLOW DISPOSABLE DIAPER OPENINGS AND RE-FASTENINGS

This is a continuation of application Ser. No. 709,748, filed July 29, 1976, now abandoned.

BACKGROUND OF THE INVENTION

This invention relates to disposable diapers of the type having adhesive closure tabs for fastening purposes, and in particular concerns a separate element which may be added to adhesive closure tabs in order to provide a system that may be opened after fastening, and then re-closed.

One of the problems that has been encountered in the use of adhesive closure tabs on disposable diapers is the tearing which readily occurs when attempts are made to re-position the tapes during fastening, or if the diaper needs to be opened to check for soiling. Especially in situations arising during toilet training of toddlers is this problem bothersome and expensive. For instance, each time the diaper has to be removed for training purposes the tapes must be peeled from the thin plastic outside film. Too often this peeling tears the film with the consequence that a possibly unsoiled diaper cannot be used again, or some inconvenient patch-up attempts are made to salvage the diaper. Loss of this unsoiled diaper, and others like it, adds up to an economic and environmental burden.

While there have been recent attempts to overcome this problem, the previous efforts were concerned with supplying an adhesive closure system which the manufacturer supplies with the disposable diaper and which, in some way, allows for more than one opening and re-closing of the diaper. For instance, such a closure system for opening and refastening diapers is described in U.S. Pat. No. 3,951,149. In that patent the separable tape comes with the fastening tape as part of the system. On the other hand, there are many disposable diapers on the market which have no means to allow ready separation from the fastened condition for diaper opening. It is primarily to these diapers that this invention is directed.

SUMMARY OF THE INVENTION

As a result of the present invention, disposable diapers with the well-known adhesive closure tabs can be readily and conveniently modified in order to allow easy separability of the tape tab from the diaper surface after an original fastening has been made. This new invention is adaptable to most all of the standard and market accepted tape tabs, and comes as a separate, individualized element for each tape tab. In addition to its widespread adaptability on various tape tabs, the principal advantage of this invention lies in the facilitation of separating the adhesive tape from the diaper surface to check the diaper, reposition the tape and the like. This separation of tape from diaper is accomplished without tearing the diaper surface. In this regard, a diaper may be opened to re-position the tapes for a neater fit during diapering, to check for soiling inside after use, and may be used over again, if not soiled, especially during toilet training periods. The result of this separability feature is the savings experienced in not having to discard unsoiled diapers due to torn outside surfaces or unusable adhesive tabs.

In accordance with the principles of this invention a separability member such as a tape, is used in combination with the adhesive portion of a closure tab on a disposable diaper to allow separation of the closure tab from the diaper, and to allow re-fastening of the tab to the diaper. This separability member includes a strip of material having a shape and size generally and preferably the same as the adhesive portion of the adhesive tape tab. The strip of material has a non-adhesive surface for mating with the adhesive portion of the closure tab, and an adhesive surface for fastening the strip to the diaper. On the end portions of the non-adhesive surface there are adhesive release areas to facilitate peeling of the adhesive closure tab from the strip for separation purposes. After the diaper has been fastened around a wearer the adhesive portion of the tab is detachable from the separability member by peeling the two apart with the separability member remaining affixed to the diaper after separation.

BRIEF DESCRIPTION OF THE DRAWINGS

These and other advantages, features and aspects of the invention will become apparent upon reading the following detailed description and upon reference to the accompanying drawings, wherein:

FIG. 1 is a perspective view of the preferred separability member;

FIG. 2 is a sectional view showing the separability member located on the adhesive portion of a disposable diaper closure tab previous to the original fastening of the diaper;

FIG. 3 shows a diaper with one corner conveniently opened; and

FIG. 4 is a sectional view depicting another embodiment of the combined adhesive closure tab and separability member.

While the invention will be described in connection with a preferred embodiment, it will be understood that it is not intended to limit the invention to that embodiment. On the contrary, it is intended to cover all alternatives, modifications, and equivalents as may be included within the spirit and scope of the described invention.

DETAILED DESCRIPTION OF THE INVENTION

With reference to FIGS. 1-3 of the drawings wherein a preferred embodiment of the present invention is illustrated, there is shown a separability member 10. Separability member 10 is added to the adhesive portion of diaper closure tabs in order to modify those tabs to allow easy tape separation from a surface of the diaper. As seen in FIG. 2, a typical disposable diaper 11 is constructed of a fluid pervious inner surface 12, a fluid impervious outer surface 14, such as a thin, flexible plastic film, and between the surfaces is an absorbent layer 15 comprised of pulp, fluff and the like. This diaper 11 includes an adhesive closure tab 16, one end portion of which is permanently secured to the diaper such as by adhesive means 18. Extending beyond the edge of the diaper is the fastening or adhesive portion 19 of the tab which in the typical and well-known disposable diapers, fastens the diaper around the wearer thereof, as better seen in FIG. 3.

In order to provide the separability or detachable features described above, separability member 10 is used in combination with the adhesive portion 19 of the tab. Separability member 10 includes a strip of material, in this case a tape 20, which has a non-adhesive surface 21 and a surface with an adhesive layer 22 deposited thereon. Non-adhesive surface 21 has on each of its ends adhesive release areas 24 and 25. For the most efficient use of typical adhesive closure tabs, tape 20 has a shape and size generally the same as that of the adhesive portion 19 of the tab. Tapes 20 with a length of 1 5/16 inches (3.33 cm.) and a width of ¾ inch (1.90 cm.) are common and are adaptable to many of the adhesive closure tab diapers on the market today. For best results and practice of this invention the thickness of tape 20 may range from about 0.002 inches (0.0051 cm.) to about 0.012 inches (0.0306 cm.).

Referring to FIG. 2, separability member 10 is shown in combination with the adhesive portion 19 of the closure tab. The non-adhesive surface 21 is mated with the adhesive material 18 on the adhesive portion 19. Adhesive release areas 24 and 25 are also mated in face to face relationship with the adhesive layer 18. Although it appears from FIG. 2 that the adhesive release areas 24 and 25 lift tape 20 from the adhesive surface 18, this is merely an exaggeration in order to adequately depict those adhesive release areas. In actuality, the adhesive release areas are very thin so that the remainder of the non-adhesive surface 21 of the tape 20 lies upon and in contact with the adhesive material 18. In this structural relationship of the tapes just described, adhesive layer 22 on the separability tape 20 is exposed, and it is this adhesive material which is used to make the original fastening of the diaper around the wearer.

A partially fastened and partially open diaper 11 is illustrated in FIG. 3. To fasten the diaper, the extending, adhesive portion 19 of the closure tab, carrying the separability member 10, is fastened to the outside surface 14 of the diaper. In the original fastening, the adhesive 22 of the separability tape 20 contacts the outside surface 14, with tape 20 and adhesive portion 19 remaining adhered together. This combination of closure tape and separability tape provides a good, sufficiently strong diaper closure to keep the diaper adequately fastened even around an active wearer.

After the diaper 11 has been fastened around a wearer the fastening or adhesive portion 19 of the tab is detachable from the separability member 10 by peeling the two apart. The operator merely lifts the end of adhesive portion from release area 25 and peels adhesive portion 19 from the tape 20. When peeled off, the separability member remains affixed to the outside surface 14 of the diaper. It has been found that the adhesive release areas on the ends of the separability member 10 eliminate or greatly reduce the peel forces transmitted to the diaper surface by the closure tape as it is pulled away. Since peeling is not started (or ended) at the ends of the separability member, mainly shear forces are transmitted to the diaper surface through the separability tape. As the greatest susceptibility of the plastic film surface to tearing is due to peel forces, it can be explained that reduction of peel forces significantly lowers the chances of tearing of the film surface. Thus, with the structure of the separability member, a closed diaper may be opened without tearing the diaper surface; furthermore, since no tearing occurs, the diaper may be closed again with a sufficiently strong closure.

In this embodiment being described, the adhesive release areas 24 and 25 may be strips, coatings, layers or the like of release agent of the well-known variety which are used to release an adhesive material from the surface to which they are applied. The end areas of release material refer to the marginal portions of the separability tape 20, and are those ends which lie transversely across the tape as seen in FIGS. 1–3.

To use the separability member of this invention, the diaperer starts with a clean diaper of the known type, and exposes the adhesive or fastening portion of the tape tab by lifting the tape from a release liner or by removing a release cover. The separability member is then placed on the adhesive portion of the tab as clearly shown in FIG. 2. Now, the diaper is ready for fastening around the wearer with the separability feature included.

Alternatively, instead of placing the separability member on the adhesive portion of the closure tab, it may be secured directly to the surface of the diaper at the location where the tab is to be fastened to effect a closure. The diaperer merely attaches the separability member by its adhesive surface to the diaper so that the release areas are facing up or exposed. While this alternative may be practiced, it is somewhat less reliable since the precise location on the diaper where the tape is to be fastened is not readily determinable, nor is it always at the same position on different diaperings. However, if this alternative is found convenient to some users, it most certainly falls within the purview of this invention.

While the separability member described above and in conjunction with FIGS. 1–3 is preferred since it may be used with most, if not all, of the presently known and used disposable diaper tape tabs, other embodiments of this invention are also useful and include the advantages and features of the preferred embodiment. For instance, in FIG. 4 there is illustrated a disposable diaper 30 having a fluid pervious inner surface 31, a fluid impervious outer surface or plastic film 32 and an absorbent layer 34 of pulp or fluff therebetween. A tape with a first portion 35 is secured to the outside surface 32 by a layer of adhesive material 36 thereon. A second portion 38 of the tape extends beyond the edge of the diaper, and has, on the surface facing the inner surface 31 of the diaper, a layer of adhesive material 39. Adhesive material 39, however, does not cover the entire extendable portion of the tape, but is located in the central segment of that surface. Thus, the two end segments 40 and 41 of that surface of the extendable portion 38 of tape are free of adhesive material. These adhesive free segments 40 and 41 traverse the width of the tape and vary in length. However, lengths of adhesive free segments at the ends of the extendable portion of about ⅛ inch (0.318 cm.) may be typically used.

For separability purposes, the same as outlined above, a separable tape 42 is added to the adhesive surface of the extendable portion 38 of the tape. Separable tape 42 generally has the same shape and size as the extendable portion 38 of the tape in order to make maximum use of the dimensional characteristics of the tape tab system. By having such similar dimensions, when mated with the adhesive surface 39 of the extendable portion, the ends of the separable tape 42 overlap the adhesive layer, and are thereby free of any adhesive attachment. Once again, by elimination of adhesive attachment at the ends of the two joined tapes, the forces experienced between the two are reduced to virtually only shear forces, with the tearing or peeling forces significantly reduced or eliminated. To make an attachment to the diaper, the exposed portion of the separable tape 42 has a layer of adhesive material 44 thereon. This embodiment is prepared and used in the same manner as the preferred; and after the diaper has been fastened around the wearer, the extendable portion of the tape is detachable from the separable tape by peeling the two apart. As in FIG. 3, the separable tape remains affixed to the diaper surface after separation occurs.

Thus it is apparent that there has been provided, in accordance with the invention, a separability member for use in combination with disposable diaper closure tabs that fully satisfies the aims, advantages and aspects as set forth above. While the invention has been described in conjunction with specific embodiments thereof, it is evident that many alternatives, modifications and variations will be apparent to those skilled in the art in view of the foregoing description. Accordingly, the plenary invention is intended to embrace all such alternatives, modifications and variations as fall within the broadest spirit and scope of the described invention.

What is claimed is:

1. In combination with the disposable diaper of the type having a thin, flexible plastic film outer surface and having adhesive closure tabs; a separability member for use with the adhesive portion of a closure tab to allow separation of said closure tab from said diaper and re-fastening thereto without tearing the diaper outer surface, said separability member comprising: a strip of material having a non-adhesive surface for mating with the adhesive portion of said closure tab and an adhesive surface for fastening said strip to the diaper outer surface; and adhesive release areas on the end portions of the non-adhesive surface of said strip, whereby after said diaper has been fastened around a wearer thereof, said adhesive portion of the tab is detachable from said separability member by peeling the two apart without tearing the diaper outer surface due to the reduction or elimination of peel forces transmitted to the diaper surface at the end portions of said strip by the provision of said release areas, the separability member remaining affixed to the diaper after separation for subsequent re-fastening.

2. The combination of claim 1 wherein said strip of material is a strip of tape.

3. The combination of claim 1 wherein said strip has a shape and size generally the same as that of said adhesive portion of said tape.

4. The combination of claim 1 wherein said adhesive release areas are strips of release material.

5. The combination of claim 1 wherein said adhesive release areas are coating of release material on ends of said strip.

6. The combination of claim 1 wherein said adhesive release areas on the ends of said strip are coated with release material.

* * * * *